United States Patent [19]

Spelsberg

[11] Patent Number: 4,806,464

[45] Date of Patent: Feb. 21, 1989

[54] NUCLEAR BINDING ASSAY FOR STEROID RECEPTOR FUNCTIONALITY IN CANCEROUS CELLS

[75] Inventor: Thomas C. Spelsberg, Rochester, Minn.

[73] Assignee: Mayo Foundation for Medical Education and Research, Rochester, Minn.

[21] Appl. No.: 13,569

[22] Filed: Feb. 11, 1987

Related U.S. Application Data

[63] Continuation-in-part of Ser. No. 652,295, Sep. 19, 1984, Pat. No. 4,711,856.

[51] Int. Cl.[4] ............... C12Q 1/68; C12Q 1/20; G01N 33/566; G01N 33/567
[52] U.S. Cl. ...................................... 435/6; 424/3; 424/9; 435/7; 435/29; 435/34; 436/501; 436/503; 436/504; 436/813
[58] Field of Search ............... 424/3, 9; 436/501, 503, 436/504, 813; 435/29, 34, 6, 7

[56] References Cited

U.S. PATENT DOCUMENTS

| | | | |
|---|---|---|---|
| 4,215,102 | 7/1980 | Lee | 424/3 |
| 4,232,001 | 11/1980 | Jensen et al. | 436/531 |
| 4,423,151 | 12/1983 | Baranczuk | 436/817 |
| 4,433,056 | 2/1984 | Baranczuk | 436/503 |

OTHER PUBLICATIONS

T. C. Spelsberg et al., in "Clinical Laboratory Molecular Analyses", Grune & Stratton, Inc. (1985), at pp. 189–203.
I. Jung-Testas et al., *J. Steroid Biochem.*, 20, 301 (1984).
R. R. Weichselbaum et al., *J. Cell. Physiol.*, 103, 429 (1980).
D. Huchon, *Ann. Endocrinol.*, 8, 223 (1977).
L. Laing et al., The Lancet, p. 168 (7/23/77).
A. G. Fazekas and J. K. MacFarlane, The Lancet, p. 565 (1982).
R. E. Leake et al., *Brit. J. Cancer*, 43, 59 (1981).
S. G. Korenman, *J. Clin. Endocrinol. Metab.*, 28, 127 (1968).
K. J. Andersen et al., *Anal. Biochem.*, 83, 703 (1977).
M. L. Graham, II et al., *Mayo Clin. Proc.*, 59, 3 (1984).
P. A. Boyd et al., *Biochem.*, 18, 3685 (1979).
P. A. Boyd-Leinen et al., *Endocrinology*, 111, 30 (1982).
P. A. Boyd-Leinen et al., *J. Biological Chem.*, 259, 2411 (1984).
A. Geier et al., *J. Endocrinol.*, 80, 281 (1979).
T. Thorsen, *J. Steroid Biochem.*, 10, 661 (1979).
A. G. Fazekas et al., *J. Steroid Biochem.*, 13, 613 (1980).
J. K. MacFarlane et al., *Cancer*, 45, 2998 (1980).
T. Thorsen and K. F. Stoa, *J. Steroid Biochem.*, 10, 595 (1979).
Holdaway et al., *Cancer*, 52, 479 (1983).
Okret et al., *Cancer Res.*, 38, 3904 (1978).
Duvivier et al., *Clinica Chimica Acta*, 112, 21 (1981).
K. Burton, *Biochem. J.*, 62, 315 (1956).

*Primary Examiner*—Christine M. Nucker
*Attorney, Agent, or Firm*—Merchant, Gould, Smith, Edell, Welter & Schmidt

[57] ABSTRACT

A method for rapidly determining the presence of functional cellular steroid receptors by assaying a tissue sample for nuclear steroid or antisteroid binding is disclosed which comprises treating the tissue with collagenase, incubating the isolated cells with a labelled steroid or a labelled antisteroid capable of complexing said receptors and measuring the bound nuclear radioactivity and the DNA of the isolated cellular nuclei.

37 Claims, 7 Drawing Sheets

(Receptor Quantitation)

(Receptor Function)

Nuclear Binding of [³H] Progesterone and [³H] Estradiol in Normal Endometrium Using the BNB Assay

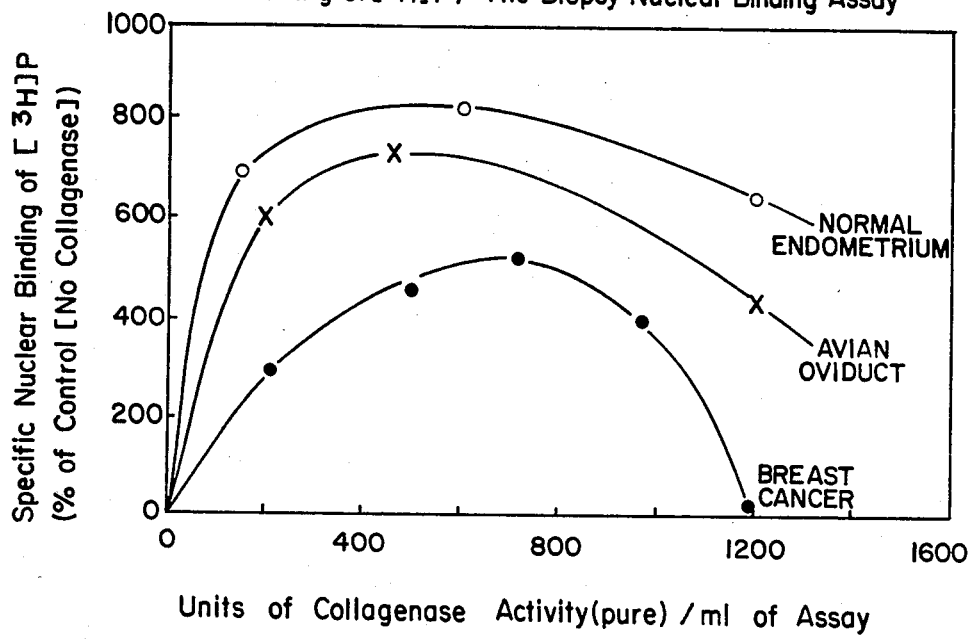
FIG. 4 Composite of Effects of Collagenase Treatments on Nuclear Binding of [³H]P; The Biopsy Nuclear Binding Assay
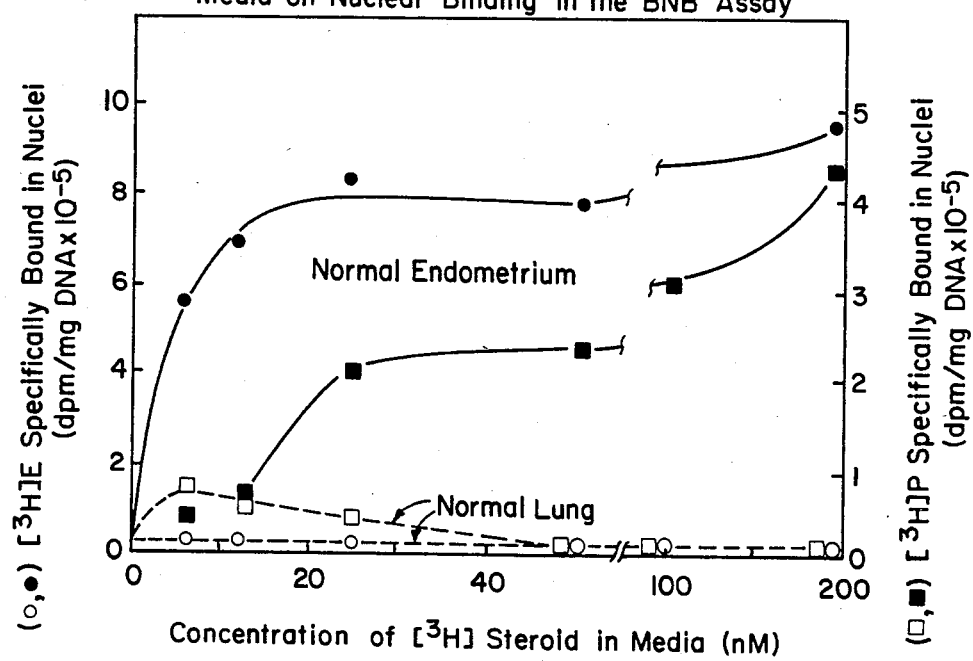
FIG. 5 Effect of [³H]E and [³H]P Concentrations in Media on Nuclear Binding in the BNB Assay

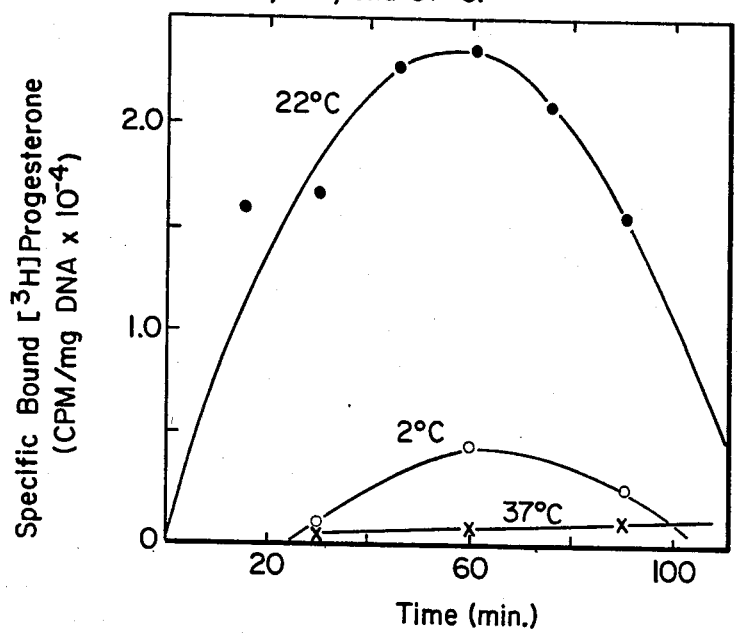
FIG. 6  Nuclear Binding of [³H]Progesterone in Tissue Culture of Normal Endometrium at 2°, 22°, and 37°C.
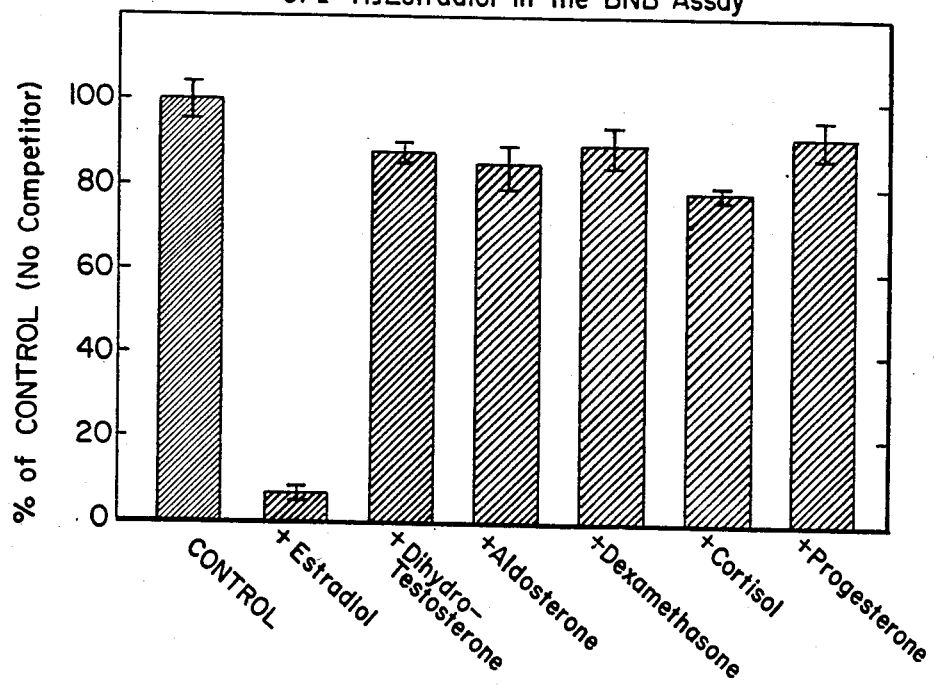
FIG. 7  Steroid Specificity of the Nuclear Binding of [³H]Estradiol in the BNB Assay Reproducibility of the Tissue Culture Assay for Functional Receptors

NUCLEAR BINDING ASSAY FOR STEROID RECEPTOR FUNCTIONALITY IN CANCEROUS CELLS

CROSS-REFERENCE TO RELATED APPLICATION

This application is a continuation-in-part of application Ser. No. 652,295, filed Sept. 19, 1984 now U.S. Patent No. 4,711,856.

FIELD OF THE INVENTION

The invention pertains to a cell culture assay for the determination of functional steroid receptor proteins in cells, and is specifically useful to determine the susceptibility of cancer cells from human tissue to steroid or antisteroid therapy.

BACKGROUND OF THE INVENTION

Cancer is a leadng cause of death, second only to heart disease, of both men and women. In the fight against cancer, numerous techniques have been developed and are the subject of current research, directed to understanding the nature and cause of the disease, and to provide techniques for control or cure thereof.

Since most cancers occur in tissues which are steroid target tissues, treatments using steroid therapy have been useful. Some steroids (e.g., progesterone, glucocorticoids) and antisteroids (e.g., the antiestrogen, tamoxifen) inhibit cell division in most cells. The use of pharmacologic doses of estrogens, antiestrogens or reduction of estrogen (by ablative surgery) have also proven to be effective therapies for the control of breast cancer. For example, the nonsteroidal antiestrogen, tamoxifen, competes with estrogens for cytosol estrogen receptors and thus blocks the effects of extrogen in the target tissue. Progestins have been used to treat endometrial cancer and glucocorticoids have been used to treat leukemias.

Despite the above, it has been found clinically that within each class of cancer, certain populations do not respond to steroid or to antisteroid therapy. Much research has been directed to determining why this is so, both to provide a clinical diagnostic tool so that time will not be lost on steroid or antisteroid therapy for those patients having cancers that will not respond, and also to provide insight into the nature of the disease.

A known difference between steroid "target" and "nontarget" tissues is the presence of specific receptor proteins for steroids in target cells which serve as intermediaries in the action of these hormones. The generally accepted mechanism of action of steroids or antisteroid compounds in target cells is (1) entrance of the compound into cells and binding of this compound to specific receptor proteins, (2) activation of the receptor and the TCS translocation and binding of this steroid receptor complex from somewhere in the cytoplasma or nucleus to the nuclear acceptor sites on the chromosomal material, (3) alteration of transcription of a multitude of genes into messenger RNA (mRNA), (4) processing of the mRNA, and (5) translation of these mRNAs into proteins which perform or serve a variety of functions.

Procedures have been developed to assay for the presence of these receptor proteins. In approximately 20% of cancers from steroid target tissues that have been studied, the steroid receptors are very low in concentration or are absent. As expected, these particular cancers do not respond to steroid therapy. Patients with negative receptor assays also do not respond to non-steroidal antisteroids such as tamoxifen.

However, in studies of steroid therapy in receptor-positive cancer patients, only about half of these cancers (approximately 40% of all cancers) respond to steroid therapies. Examples of this are found in tamoxifen treatments of breast cancers and progesterone treatment of endometrial cancers. It has been speculated that the defects in the steroid action pathway are related to steps subsequent to the binding of the steroid to its receptor.

That defective (nonfunctional) receptors occur and may play a role in the nonresponse of many breast cancers of steroid therapy was reported by Leake and co-workers. As used herein with respect to receptors, the term "nonfunctional" indicates receptors incapable of activation and binding to chromosomal material. Such receptors can bind steroids or antisteroids but are otherwise defective with respect to the steroid action pathway. Studies by this group reported that 25 to 30% of 461 estrogen receptor (ER)-positive breast tumors showed no nuclear estrogen receptor (ERN), i.e., the receptors were nonfunctonal (Laing et al., *Brit. J. Cancer*, 43, 59 (1977); Leake et al., *The Lancet*, 168 (1981)). In these studies, the cytosol estrogen receptor (ERC) was isolated from the tumors and the standard charcoal receptor quantitation assay performed according to the method of S. G. Korenman, *J. Clin, Endocrinol. Metab.*, 28, 127 (1968). The ERN was assayed by incubating the nuclear pellet obtained from homogenized tissue with [$^3$H]-estradiol and determining the amount of ERN present. Similar results were obtained in another laboratory using an in vitro system by incubating crude [$^3$H]-ERC with isolated nuclei and assaying th salt-extracted radioactivity (Fazekas and MacFarlane, *The Lancet*, 565 (1982)). In both studies, a 75 to 100% correlation was found between the presence of a nuclear receptor (i.e., presence of a functional receptor) and the tumor response to steroid therapy.

T. Thorsen et al., *J. Steroid Biochem.*, 10, 595 (1979) disclose a non-quantitative assay for the presence of functional nuclear steroid receptors involving the incubation of whole tissue slices with non-saturating amounts of [$^3$H] estradiol.

Thus, assays effective to measure functional/non-functional steroid receptors allow a more accurate prediction of which patients will or will not respond to steroid or to antisteroid treatment than do assays which simply determine the presence or absence of receptors. Reliable assays of this type will greatly assist the clinician in planning a course of treatment for these patients and would avoid the loss of treatment time due to the use of ineffective therapy. Although the Leake and MacFarlane methods have demonstrated success in discriminating between functional and nonfunctional nuclear receptors, a need exists for improved nuclear binding assays which the functionality of (a) are able to analyze all of the receptors in a cell (b) do not require the isolation of the nuclear receptor, (c) do not require cell-free incubations, (d) require less tissue and/or (e) can be performed rapidly with readily-available equipment.

BRIEF DESCRIPTION OF THE INVENTION

The present invention is directed to a cell culture assay which can rapidly and accurately identify whether or not tumor cells have functional steroid receptors. The method measures the amount of nuclear-bound steroid or antisteroid in the cells. This assay gives the investigator a rapid indication as to how much biologically-active receptor is present per mg DNA or per cell. The assay requires significantly less tissue and is believed to be more rapid than those assays requiring receptor isolation and quantitation or than those involved in measuring receptor translocations in a cell-free system. The assay may be referred to herein as the "biopsy nuclear binding assay" or "BNB."

In its broadest embodiment, the present method comprises:

(a) fragmenting a tissue sample, such as a sample of carcinoma tissue; into pieces containing intact cells (b) digesting said fragmented tissue with collagenase;

(c) isolating the cells from said digested tissue;

(d) incubating said cells with an amount of a radiolabelled steroid or a radiolabelled antisteroid capable of complexing with and saturating the cellular steroid receptors;

(e) isolating the cellular nuclei; and (f) measuring the bound radioactivity and the total DNA of said nuclei.

As used herein, the term "steroid" is intended to refer to those biologically-active, natural or synthetic, polycyclic compounds which comprise a fused-reduced or partly-reduced, 17-carbon, 4-ring system cyclopentanophenanthrene. Most steroids also have two methyl groups and an aliphatic side chain attached to the nucleus. The length of the side chain varies, and generally contains 8, 9 or 10 carbon atoms in the sterols, 5 carbon atoms in the bile acids, 2 in the adrenal cortical steroids, and none in the estrogens and androgens. Known steroids which are derivatives of costisol, progesterone, testosterone and estradiol are listed in *Steroid-Cell Interactions*, R. J. B. King, et al, eds., University Park Press, Baltimore, MD (1974), at pages 391–395, the disclosure of which is incorporated by reference herein. Steroids employed to study the specificity of cellular estrogen, progestin, androgen, mineralcorticoid and glucocorticoid receptors are listed in J. Delettre et al., *J. Steroid Biochem.*, 13, 45–59 (1980), the disclosure of which is incorporated by reference herein. Commercially-available steroids are listed in Sigma Price List, Biochemical and Organic Compounds, Sigma Chem. Co., St. Louis, Mo. (Feb. 1986) at pages 59–64.

As used herein, the term "antisteroids" refers to compounds which do not possess the cyclopentanophenanthrene ring system of the steroids, but which are capable of significant binding to functional cellular steroid receptors. Therefore, the term "antisteroid", as used herein, is intended to encompass compounds which possess both steroidal activity as well as those which are "antihormonal", i.e., which act to inhibit the activity of steroids. Many of these antisteroids, such as the anti-estrogens, are formally derivatives of stilbene, 1,2-diphenylethane, and di- and tetrahydronaphthalenes.

Known stilbene-type antisteroids include the tamoxifen, cis- and trans-clomiphene, 1-nitro-1-phenyl-2-(4-hydroxyphenyl or anisyl)-2-[4-(2-pyrrol-N-ylethoxy)-phenyl] ethylene (CN-55,945), trans-1,2-dimethyl-1,2-(4-hydroxyphenyl)ethylene (trans-dimethylstilboestrol), trans-diethylstilboestrol, and 1-nitro-1-phenyl-2-(4-hydroxyphenyl)-2-4-(3-dimethylaminopropyloxy) (GI-680).

Known 1,2-diphenylethane-type antisteroids include cis-1,2-anisyl-1-[4-(2-diethylaminoethoxy) phenyl]ethane (MRL-37), 1-(4-chlorophenyl)-1-[4-(2-diethylaminoethoxy)phenyl]-2-phenyl ethanol (WSM-4613); 1-phenyl-1,4-(2-diethylaminoethoxy)phenyl]-2-anisyl-ethanol (MER-25); 1-phenyl-1-[4-(2-diethylaminoethoxy)phenyl)-2-anisyl-ethane, mesobutoestrol (trans-1,2-dimethyl-1,2-(4-hydroxyphenyl)-ethane), meso-hexestrol, (+)hexestrol and (−)-hexestrol.

Known napthalene-type antisteroids include nafoxidine, 1-[4-(2,3-dihydroxypropoxy)phenyl]-2-phenyl-6-hydroxy-1,2,3,4-tetrahydro-naphthalene, 1-(4-hydroxyphenyl)-2-phenyl-6-hydroxy-1,2,3,4-tetrahydronaphthalene, 1-[4-(2-pyrrol-N-ylethoxy)-phenyl]-2-phenyl-6-methoxy-3,4-dihydronaphthalene (U11,100A), and 1-[4-(2,3-dihydroxypropoxy)phenyl]-2-phenyl-6-methoxy-3,4-dihydronaphthalene (U-23,469).

Known antisteroids which do not fall any where within these structural classifications include coumestrol, biochanin-A, genistein, methallenestril, phenocyctin, and 1-[4-(2-dimethylaminoethoxy)phenyl]-2-phenyl-5methoxyindene (U,11555).In the nomenclature employed hereinabove, the term "anisyl" is intended to refer to a 4-methoxyphenyl group.

The pharmaceutically-acceptable inorganic and organic acid amine salts of the amino group-containing antisteroids are also included within the scope of the term "antisteroid", as used herein, and include citrates, tartrates, acetates, hydrochlorides, hydrosulfates and the like.

The binding affinities of these compounds to steroid receptors relative to the binding of the "natural" steroid varies widely. For example, the antisteroid compounds listed hereinabove have been primarily characterized in terms of their antiestrogenic activity. While meso-hexestrol exhibits three times the binding affinity of estradiol to estrogen receptors in rat cytosol, compound U23,469 exhibits only about 40% of the binding affinity of estradiol to estrogen receptors in the same competition assay.

DETAILED DESCRIPTION OF THE INVENTION

Figure 1:
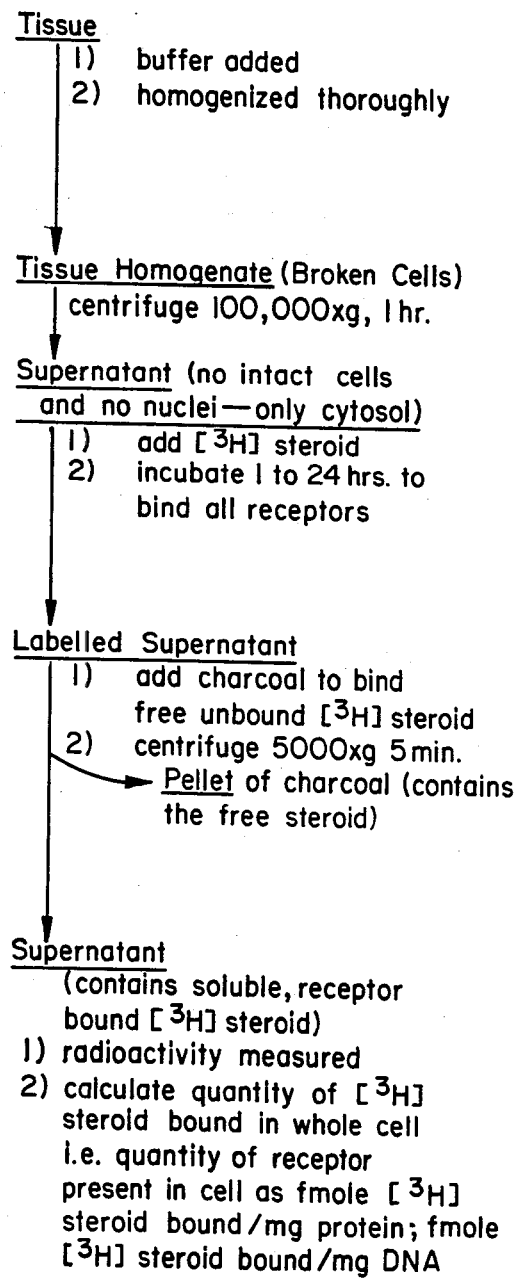

According to the method of the present invention, the tissue to be assayed is treated with collagenase under controlled conditions. The cells are isolated intact and incubated with the appropriate radiolabelled steroid or antisteroid. The cellular nuclei are isolated, and the bound steroid or antisteroid measured. The nuclei obtained from surgical biopsies of 10 mg (wet wt.) or more are then hydrolyzed and assayed for DNA by a standard method such as the diphenylamine assay. Alternatively, when using very small tissue samples, half of the nuclei are not filtered but are used for the measurement of the DNA by a fluorescence assay (ethidium bromide). The latter assay is about 50 times more sensitive than the diphenylamine method. Since DNA quantitation is the limiting factor when using very small biopsies, utilization of the fluorescence method allows 1 to 5 mg biopsy sections to be analyzed for both functional receptors and DNA.

In practice of the present invention, normal and diseased tissue is obtained, for example, from surgical biopsies from patients with normal endometrium, from patients with previously untreated endometrial carcinomas and from patients with breast carcinomas. Cells may also be obtained from cell cultures or from blood. In the examples, all normal endometrium and lung and most carcinomas were obtained from post-menopausal female patients. Following appropriate histologic assessment, representative biopsy samples are placed in sterile buffers at ambient temperature for immediate use in the present nuclear binding assay, preferably within 2 hours of surgery. Biopsies, frozen within this time and stored at −80° C. for up to two weeks can also successfully be assayed. Any excess tissue can be cryopreserved for the previously-developed, standard receptor quantitation assay.

Biopsy samples from human tissue are transferred to a suitable nutrient medium and fragmented, e.g., by mincing or chopping. The resultant tissue fragments are weighed, and transferred to a nutrient medium containing collagenase. A fixed ratio of about 0.5–15 units of collagenase, preferably about 1–5 units of collagenase per mg tissue, is preferred for reduction of all tissue types. The fragments are gently disrupted and filtered. Any retained tissue is again incubated with fresh collagenase. Following a second gentle disruption, the suspension is again filtered. Cells in the filtrate are pelleted by centrifugation and washed.

The final cell pellet is resuspended in a nutrient medium for the incubations with radiolabelled steroids or antisteroids. Radiolabelled steroids and antisteroids may be produced by a wide variety of synthetic techniques which are well known in the art. Methods for labelling steroids and antisteroids with deuterium and tritium are set forth in *Methods in Enzymology*, S. P. Colowick et al., eds., Academic Press, N.Y. (Vol. IV, 1957) at pages 732–737, the disclosure of which is incorporated by reference herein. Such techniques include the platinum-catalyzed exchange or carbon-bound hydrogen by deuterium or tritium in solutions for suspensions of the steroid or antisteroid in $D_2O$ or $T_2O$. Tritiated steroids or antisteroids can also be prepared by the hydrogenation of suitablysubstituted steroids or antisteroids, e.g., those comprising halogen, CH=CH or —S— moieties. Chemical reduction reactions using tritiated metal hydrides can also be employed and ketonic compounds can be enolyzed in the presence of $T_2O$ and alkali. Tritium water has been employed for the biosynthetic preparation of steroids containing tritium in amounts adequate for further biological assays.

A wide range of additional labelling techniques are disclosed in Feteanu et al., "Labeled Antibodies in Biology and Medicine", pages 214–309 (McGraw-Hill Int. Book Co., New York (1978)). The introduction of various metal radioisotopes may be accomplished according to the procedures of D. J. Hnatowich et al., *Science*, 220, 613 (1983); Wagner et al., *J. Nucl. Med.*, 20, 428 (1979); Sundberg et al., *J. Med. Chem.*, 17, 1304 (1974); and Saha et al., *J. Nucl. Med.*, 6, 542 (1976).

Among the radioisotopes used, x-ray-emitters, gamma-emitters, positron-emitters, and fluorescence-emitters are suitable for receptor quantitation, while beta-emitters and alpha-emitters can also be used for therapy. Suitable radioisotopes for labelling steroids or antisteroids include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Scandium-47, Tellurium-121m, Tellurium-122m, Tellurium-125m, Thulium-165, Thulium-167, Thulium-168, Technetium-99, Copper-67, Fluorine-18, Yttrium-90, Gold-199, Palladium-100, Bismuth-217 and Antimony-211. Preferred radioisotopes for labelling compounds intended for use as therapeutic as well as receptor quantitation agents include Iodine-125, Iodine-131, Yttrium-90, Gold-199, Palladium-100, Copper-67, Bismuth-217 and Antimony-211.

One useful technique for labelling the steroidal D-ring with radioactive halogen atoms employs halogen exchange as described by R. B. Hochberg, *Science*, 205, 1138–1140 (1979) and R. B. Hochberg et al., *PNAS USA*, 77, 328–332 (1980). Acetylated steroids can be directly halogenated and reduced to yield radiolabelled compounds by the method of J. A. Katzenellenbogen et al., *J. Nuclear Med.*, 23, 411–419 (1982). Halogenation of steroidal A-rings can be accomplished by mixing them with N-chlorosuccinimide (NCS) and radioactive alkali metal halogen salts as disclosed by D. S. Wilbur et al., *J. Org. Chem.*, 47, 359–362 (1982), and references cited therein.

Other useful labelling techniques involve labelling with either Iodine-131 (I-131) or Iodine-125 (I-125) using oxidative procedures wherein a mixture of radioactive potassium or sodium iodide and the steroid or antisteroid is treated with chloramine-T (N-chloro-p-toluene sulfonamide sodium salt) e.g., as reported by Greenwood et al., in *Biochem. J.*, 89, 114 (1963) and modified by McConahey et al., in *Int. Arch. Allergy Appln. Immunol.*, 29, 185 (1969).

The media of replicate assays are made about 5–50 nM in labeled steroid or antisteroid, e.g, about 10–30 nM in [$^3$H] progesterone (or [$^3$H] estradiol). Parallel duplicate incubations are typically performed with about 10–20 nM of labelled steroid or antisteroid, e.g., [$^3$H] progesterone and an excess of the corresponding unlabelled steroid or antisteroid, e.g., progesterone (or at least about 10–20 nM [$^3$H] estradiol and excess unlabelled estradiol) to determine the extent of nonspecific binding. Incubations may be carried out at about 18°–25° C. for about 0.5–1.5 hour, preferably at about 22° C. for 1.0 hr.

After the incubations, the tubes are chilled to about 0°–10° C. and mixed with cold neutral medium (e.g., 5 mM HEPES buffer). The cells are sedimented by cold centrifugation. The cellular pellet is then subjected to a micronuclear isolation method which may readily be adapted to a routine clinical laboratory setting. The cells are homogenized in a cold, neutral buffer, preferably a sucrose or glycerol-KCl-Tris-Triton-X-100 (octoxynol-9, Rohm & Haas) medium. The homogenate is layered over a cold, neutral medium containing sucrose, glycerol, Triton X-100, Tris-HCl (tris(hydroxymethyl)amino-methane hydrochloride) and KCl. The tubes are centrifuged in the cold. The pellet of partially purified nuclei is resuspended in a neutral solution. An aqueous solution comprising Tris-HCl and aqueous glycerol using a weight ratio of medium to starting tissue of about 1:0.05–0.15, preferably about 1 ml per 100mg starting tissue is useful for this purpose.

The nuclei are then analyzed for nuclear binding of the [$^3$H] steroid or labelled antisteroid by collecting them on filters which were dried and assayed for DNA by acid hydrolysis of the filters and quantitating the solubilized nucleotides by the diphenylamine assay of Burton as set forth in *Biochem. J.*, 62, 315 (1956), the disclosure of which is incorporated by reference herein. The hydrolyzed filters are then measured for radioactivity. This method allows the measurement of the total DNA and the bound radioactivity.

Alternatively, the nuclei are sedimented into pellets, the pellets are extracted with absolute ethanol for one hour, and the nuclei are resedimented. The alcohol extract is assayed for radioactivity and the pellet assayed for DNA by a diphenylamine "mini-assay" which can detect 0.1–5 µg of DNA per assay. (See below)

The [³H] steroid or labelled antisteroid specifically bound in the nuclei is expressed as CPM/mg DNA, as DPM/mg DNA, as fmol/mg DNA or as molecules/cell nucleus. The specific binding is obtained by subtracting the nonspecific binding from the total binding. The [³H] steroids or antisteroids are not removed by the acid hydrolysis.

For the microassay of nuclear binding, which can be carried out with an initial portion of about 1–5 mg of tissue, the DNA is quantitated by the ethidium bromide fluorescene method of U. Karsten et al., *Anal. Biochem.*, 40, 135 (1972) and K. J. Anderson et al., *Anal. Biochem.*, 83, 703 (1977). In this method, aliquots of the nuclei containing about 0.5–5 µg DNA are isolated prior to filtration and treated with a protease (Pronase) and ribonuclease. The aliquots are cooled, mixed with ethidium bromide and the fluorescence determined.

Alternatively, the diphenylamine assay was modified to yield a "mini-assay", capable of detecting and quantitating 0.1 µg to 5 µg DNA per assay tube. The method involves the extraction of the radioactive steriod from the nuclear pellet with 1.0 ml absolute ethanol containing 0.25M sodium acetate for one hour. The solution is centrifuged at 6000× g for 10 min. and the alcohol supernatant is counted in a scintillation counter. The DNA in the residual nuclear pellet is then quantitated by resuspending the pellets in 0.1 ml of 0.5N perchloric acid and heating the suspension for 15 min. at 90° C. The Burton diphenylamine reagent (0.2 ml) is then added and the reaction mixture is covered and incubated for 18.0 hr. in the dark. The reaction mixture is then transferred to microtube plates and the absorption is read in a micro titre plate reader to quantitate the DNA.

The level of nuclear bound radiolabelled steroid or antisteroid required for a therapeutic tumor response to steroid or antisteroid treatment can be estimated by; a) measuring a biological response to various concentrations of unlabelled steroid or antisteroid under similar conditions of incubation as described above, and assessing the level of nuclear-bound steroid or antisteroid using the same concentration of radiolabelled steroid or antisteroid. (The particular biological response will dictate the length of exposure required for the unlabelled steroid or antisteroid. The incubation of cells with the radiolabelled material should remain at 60 min), b) using published reports on the normal or required concentration of steroid receptor per cell nucleus for biological responses in vivo. Typical values are approximately 1000 molecules bound per cell nucleus for minimal responses and approximately 4000 to 10,000 molecules per cell nucleus for maximal responses, or c) the minimal levels of nuclear binding required for clinical response to steroid or antisteroid therapy can be more accurately determined at the end of the clinical trials. (Each responding/nonresponding tumor can be correlated with respect to its level of nuclear-bound steroid or antisteroid.)

Figure 2:
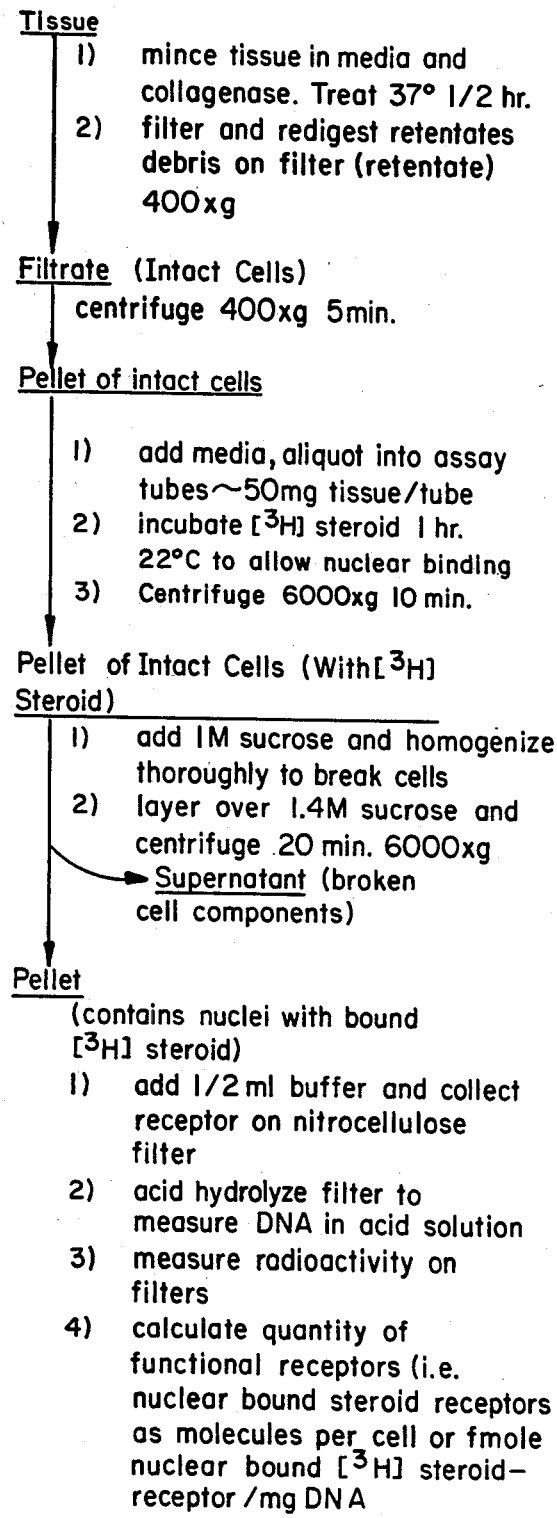

The invention will be further described by reference to the following detailed example (Example I). The conventional method is presented in detail in the Comparative Example, presented hereinbelow. The flow charts provided in FIGS. 1 and 2 are provided to facilitate a comparison between the conventional receptor quantitation method and the present BNB, respectively.

EXAMPLE I THE BIOPSY NUCLEAR BINDING ASSAY FOR FUNCTIONAL STEROID RECEPTORS

The following compounds are available from the sources indicated: Tritiated and unlabelled R5020 (dimethyl-19-norpregna-4,9-diene-3,20-dione), tritiated progesterone and estrogen (40–115 C/mmole) New England Nuclear Corp., Boston, Mass.); all other steroids and additional other chemicals are available from Sigma Co. (St. Louis, Mo.) or Fischer Scientific Co. (Pittsburgh, Pa.). All chemicals are analytical grade reagents. The steroids are routinely analyzed for degradation using high pressure liquid chromatography in a reverse phase system (uBondapak-C18 resin).

A 1.0 mg/ml collagenase enzyme preparation was used which exhibited an activity of 115–170U per ml of preparation (CS-III, Cooper Biomedical, Malvern, Pa.). One unit of activity will liberate from collagen 1 µmole of 1-leucine equivalents in 5 hours at pH 7.4 at 37° C. in the presence of the calcium ions. Ninhydrin was used to quantitate the amino acid. A. Collagenase Treatment of Tissue Biopsy samples from human tissue or chick oviducts are placed in MCDB-202 medium, pH 7.4, (K. C. Biologicals, Lemexa, Kans.) at ambient temperature and transported to the laboratory. All tissue samples are then transferred to 202 medium containing 4% w/v bovine serum albumin and finely minced. The resultant tissue fragments are collected on a nylon screen by filtration, weighed, and transferred to 202 medium containing the collagenase enzyme. A fixed ratio of 2 units of collagenase per mg tissue was employed for all tissue types. A typical experiment for tissue digestion involves placing about 400 mg tissue and 2.0 units collagenase per mg of tissue in 6.4 ml 202 medium into 25 ml Ehrlenmeyer flasks and incubating at 37° C. on a rotary shaker water bath (Precision Instruments, Chicago, IL) at 50 rpm for 30 min. The fragments are gently disrupted by drawing them in and out of a widebore automatic pipette (25 times every 15 minutes). Following the second general disruption with the automatic pipette, an equal volume of 202 medium containing 4% BSA is added. The crude suspension is filtered through nylon guaze (500×500 micron apertures) into a small glass beaker. The fragments remaining on the filter are washed with an equal volume of the 202 medium with 4% BSA. The undigested tissue on the filter is placed in fresh enzyme solution and redigested. Cells in the filtrate are pelleted by centrifugation at 50× g for 10 min and washed twice by resuspension and centrifugation in 10 ml of 202 medium with 4% BSA. The final cell pellet is resuspended in 202 medium without BSA for incubations with labeled steroids. Cell viability is determined by the Trypan blue exclusion method, which assesses the percentage of cells in the suspensions that are not permeable to the dye. In addition, the cell ultrastructure and intact membranes are examined by microscopy. The cells obtained by the above method are then assessed for nuclear binding by steroid receptors as described below. B. Incubation with [³H] Steroids The cells isolated from the collagenase treatment are resuspended in 0.2 mol 202 medium in a 12.0 ml test tube. This method can be used with cells from 1 to 50 mg biopsy specimens. The analyses are performed on cells isolated from fresh tissue within 2 hours of surgical removal as well as from frozen tissue. The assay can also be performed on tissue which has been stored a 4°

C. in 202 medium for up to 48 hours. A minimum of four incubations are performed. The medium of two duplicates is made 25 nM in [$^3$H] progesterone ($^3$H] P) (or [$^3$H] estradiol). Parallel duplicate incubations are performed with mixtures of 25 nM [$^3$H] P and 2.5 uM unlabelled progesterone (or 25 nM [$^3$H] estradiol and 2.5 uM unlabelled estradiol). All incubations are performed at 22° C. for 1 hour. For endometrial carcinomas, the progesterone receptor functionality is assessed. In breast carcinomas, both the estrogen and progesterone receptor functionalities (tissue permitting) are examined. C. Analysis of Nuclear Binding After the incubations, the tubes are chilled to 4° C. and mixed with 5 ml of a cold *Solution A* [containing 5 mM HEPES and 0.2 mM EDTA, pH 7.4 at 4° C.]. The cells are sedimented by centrifugation at 6000× g for 10 min at 4° C. The cellular pellet is homogenized in 2 ml of a cold *Solution B* [containing 10% (v/v) glycerol, 0.1% Triton X-100, 0.01 M KCl, 0.05 M Tris, pH 7.4] in a Thomas type-A glass homogenizer using a motor drive, serrated, Teflon pestle-glass homogenizer (0.001 inch clearance). The homogenate is layered over 1 ml of cold *Solution C* [containing 1.4 M sucrose 10% (v/v) glycerol, 0.2% Triton X-100, 0.05 M Tris-HCl, 0.01 M KCl, pH 7.4]. The interface between the two phases are mixed and the tubes are centrifuged for 20 min at 6000× g at 4° C. The nuclear pellet is resuspended in Solution D 50 mM Tris-HCl, 10% (v/v) glycerol, pH 7.4]. Each nuclear pellet from approximately 50 mg tissue is resuspended in 0.5 ml of Solution D. The pellets of nuclei are then analyzed for nuclear binding of the [$^3$H] steroid by resuspending the pellets in 100% ethanol for 1 hour at 22° C., and then counting the alcohol in a liquid scintillation spectrometer using a PCS-xylene fluor (Amersham-Searle, Arlington Heights, IL). The pellets are then analyzed for DNA. This method allows the measurement of both the bound radioactivity and total DNA. Specifically, the pellets are assayed for DNA by hydrolysis of the pellets in 0.5 N HClO$_4$ (90° C. for 15 min) and quantitating the solubilized nuceotides by the diphenylamine assay of Burton.

For the micronuclear binding assay, requiring less than 20 mg tissue, the DNA is quantitated by the ethidium bromide fluorescence method or by the minidiphenylamine assay described hereinabove. In the former case, aliquots of the nuclei are taken before collecting them on the filters. The aliquots of nuclei (containing approximately 0.5 to 5 μg DNA) are treated with 0.2 mg Pronase (predigested 2 hours at 37° C.) and 0.2 mg ribonuclease (predigested 10 min. at 90° C.). The nuclear aliquots are then cooled and 2.5 μg ethidium bromide is added. The solution is mixed and the fluorescence is measured on a spectrofluorometer using an excitation of 3000 Å and an emission of 5900 Å. The specifically-bound CPM/mg DNA is calculated as the difference between the assays with [$^3$H] steroid alone and those with [$^3$H] steroid +100-fold excess of unlabelled steroid.

COMPARATIVE EXAMPLE

Isolation and Quantitation of Cellular Progesterone Receptors (PR) and Estrogen Receptors (ER)

A. Quantities of Tissues Needed for the Receptor Quantitation Assay

The quantitation of the PR and ER by the Dextran charcoal method of Korenman using a one-point determination with a nonspecific control requires a minimum of approximately 500 mg of tissue for each steroid receptor. Practically all biopsies obtained from surgery are of sufficient quantity to allow (1) the nuclear binding assay of the present invention and (2) quantitation of the receptors. Of course, the quantitation of the total receptors is not required to be performed in conjunction with the nuclear binding assay.

B. Preparation of Cytosol

All experiments are performed at 4° C. Frozen tissue is stored at −80° C. for periods not longer than two months. This storage does not cause loss in receptor quantitation. The fresh and/or frozen tissue is minced, weighed, and placed in tubes in *Solution F* [50 mM Tris-HCl, 1 mM EDTA, 15 mM monothioglycerol, 10 mM sodium molybdate, 2 mM PMSF, 10% (v/v) glycerol, pH 7.4]. This buffer was shown to maintain the greatest stability in the receptor preparations with the EDTA minimizing receptor aggregation, the monothioglycerol/molybdate/glycerol stabilizing the receptor and the PMSF reducing proteolysis. Briefly, frozen surgical biopsy specimens are homogenized in a Teflon pestleglass homogenizer in 4 volumes [200 μl/50 mg tissue (wet weight)] of solution F. The sample is centrifuged at 4° C. in a Beckman Microfuge for 2 min at 10,000× g to obtain the cytosol (supernatant). The pellets are saved for DNA analysis (see below).

C. Labeling and Exchange of [$^3$H] Steroid with the Cytosolic Receptors

[$^3$H] R5020 (87 Ci/mmole) or [$^3$H] estradiol (102 Ci/mmole) in benzene/ethanol (9:1, v/v) are lyophilized and redissolved in an equal volume of absolute ethanol to achieve a 5 μM [$^3$H] steroid solution. Aliquots of this stock are added to the cytosol for 4 hours at 4° C. to give 100 nM [$^3$H] steroid, an amount sufficient to saturate the receptor sites. These conditions have also been shown to exchange practically all endogenous cold steroid with the [$^3$H] steroid. For the PR assay, cortisol is also lyophilized and redissolved in the same ethanol solution to give a 50 μm cortisol solution with the [$^3$H]P. This steroid eliminates the complication caused by R5020 binding to the glucocorticoid receptor. Aliquots of the crude cytosol are then used to quantitate the steroid receptor using the Dextran charcoal method described below.

D. Quantitation of the PR and ER Using the Dextran Charcoal Method

For each assay, 100 μl aliquots of each cytosol are incubated with [$^3$H] steroid in the presence and absence of the respective unlabeled steroid at 0° C. for 4 hours as described above. The synthetic progestin (R5020) is primarily used in the cytosol studied since it does not bind to serum-binding proteins which often interfere with assays. Standard progesterone may be used as a double check on the assay. For analysis of the progesterone receptor, one of the assays is made 100 nM [$^3$H] R5020 with 1 μM cortisol (to measure total binding) and half 100 nM [$^3$H] R5020+10 μM unlabeled R5020+1 μM cortisol (to measure nonspecific binding). For analysis of the estrogen receptor, one of the assays is made 100 nM [$^3$H] estradiol-17-beta+10 μM unlabeled estradiol. Each of the incubation mixtures are then treated with three volumes (about 500 μl) of 1% (w/w) Dextran-coated charcoal suspension (10 mg charcoal and 1 mg Dextran T-70 per ml of 1.5 mM MgCl$_2$). After a five-minute incubation at 4° C., the solutions are centrifuged at 2 min at 10$^4$× g and 250 μl of each of the supernatants measured for radioactivity (i.e., receptor bound [$^3$H] steroid). The nonspecificbond [³H] steroid (assays containing labelled and unlabelled steroid) is subtracted from the total bound [³H] steroid (assays containing only labelled steroid) to obtain specifically-bound [³H] steroid. The latter is then plotted as fmole or pmole of bound [³H] steroid per mg protein or per mg DNA for protein quantitation. For the DNA quantitation, the tissue homogenate pellets are resuspended in 0.5M NaClO₄](0.1 ml/mg tissue), incubated 90° C. for 30 min and then cooled and centrifuged 1000xg for 5 min. The supernatant is then analyzed for DNA as described above, using the diphenylamine assay.

SUMMARY OF RESULTS ACHIEVED WITH THE BIOPSY NUCLEAR BINDING (CELL CULTURE) ASSAY (BNB-ASSAY)

Figure 3:
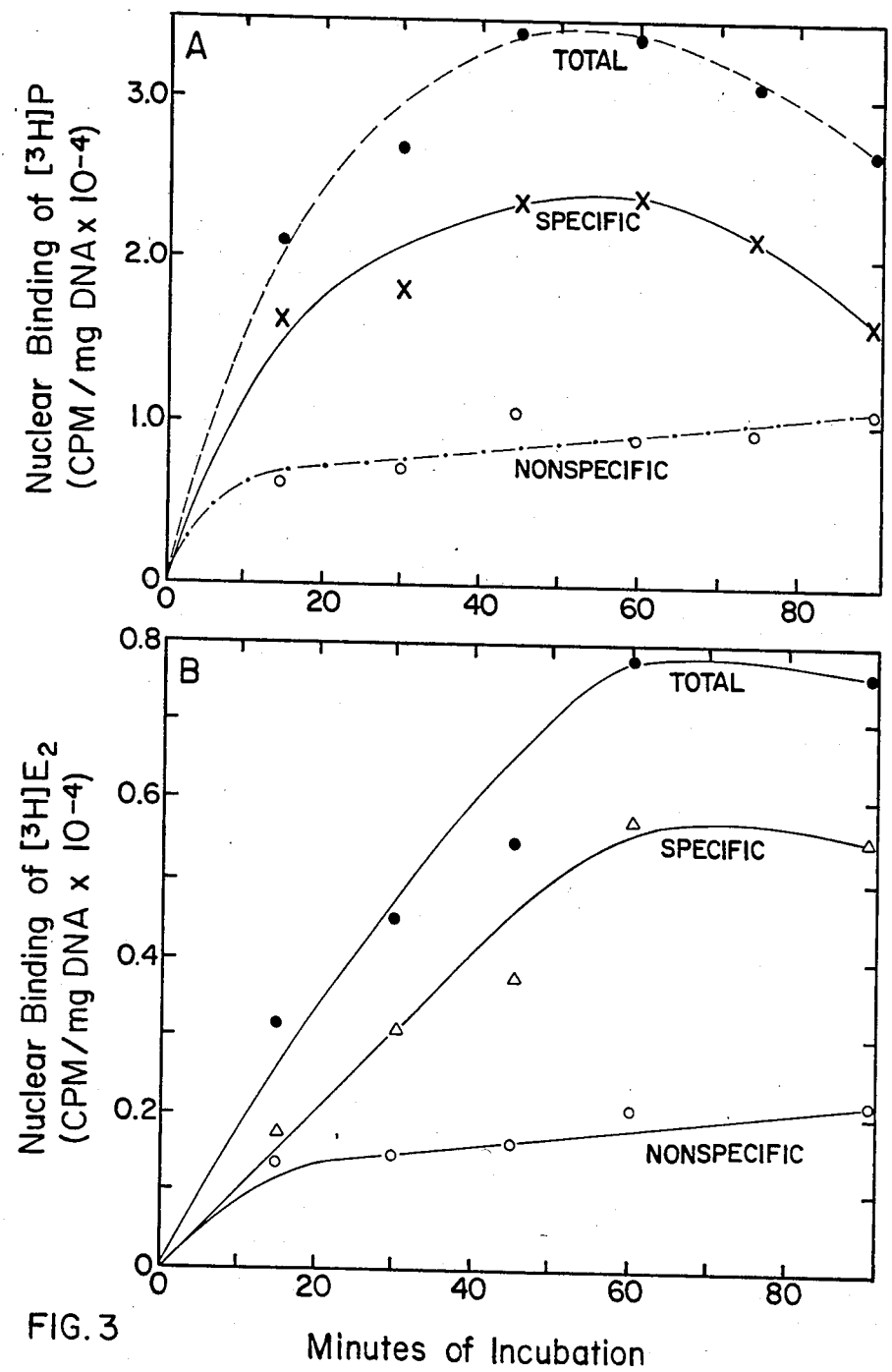

FIG. 3 shows the nuclear binding of [³H] progesterone (Panel A) and [³H] estrogen (Panel B) using the BNB assay. As described in the Example I, the nonspecific binding is subtracted from the total binding to obtain the specific nuclear binding of the steroids. The latter represents the specific receptor dependent nuclear binding of each of the steroids. Thus, a time-dependent specific nuclear binding can be measured and the 60-minute incubation period at 22° C. was found to be optimal.

FIG. 4 shows that the use of the collagenase to obtain isolated cells for cell culture in the assay significantly enhances the sensitivity of the assay (5–8 fold), over that of simple tissue culture. As shown, the collagenase treatment enhances the nuclear uptake of the steroids in the oviduct, breast cancer and endometrial tissues. Surprisingly, excessive collagenase treatments (higher concentrations) can inhibit the steroid receptor localization in the nuclei. About 50–1000 U of collagenase activity per ml of assay provides the best results.

FIG. 5 shows the effects of varying the concentrations of labelled estradiol, [³H] E, and progesterone, [³H] P, on the nuclear binding of these steroids in normal endometrium and lung. As expected, a nontarget organ (such as normal lung) shows little nuclear binding because it does not have the steroid receptors. In contrast, since the target tissue (normal endometrium) has the receptors which are functional, a marked nuclear binding is found with a maximum binding occurring at a steroid concentration in the media of around 25 nM for each steroid. Thus, a saturable, tissue-specific nuclear binding is indicated.

FIGS. 6–9 illustrate four basic properties of the nuclear binding of [³H] P and [³H] E in normal endometrium, as determined by the assay of this invention. FIG. 6 shows that at 2° C., very little specific binding occurs compared to that achieved at the 22° C. incubation. Higher temperatures show a marked inhibition of nuclear binding (e.g., 37° C.). This supports the involvement of a receptor in the nuclear binding since receptors cannot translocate and bind to nuclear sites if not allowed to "activate" as achieved by increasing the temperature over 10° C. Additional proof that a receptor is involved in the nuclear uptake of the steroid is the steroid specificity of the nuclear binding. FIG. 7 shows that only unlabelled estradiol reduces the nuclear uptake of [³H] estradiol. The same effect is observed when [³H] P is analyzed (data not shown). Thus, a steroid-specific, tissue-specific, time and temperature dependent, saturable nuclear binding of the [³H] P has been demonstrated in the present assay. These are all properties common to receptor-dependent nuclear binding of steroids.

Figure 8:
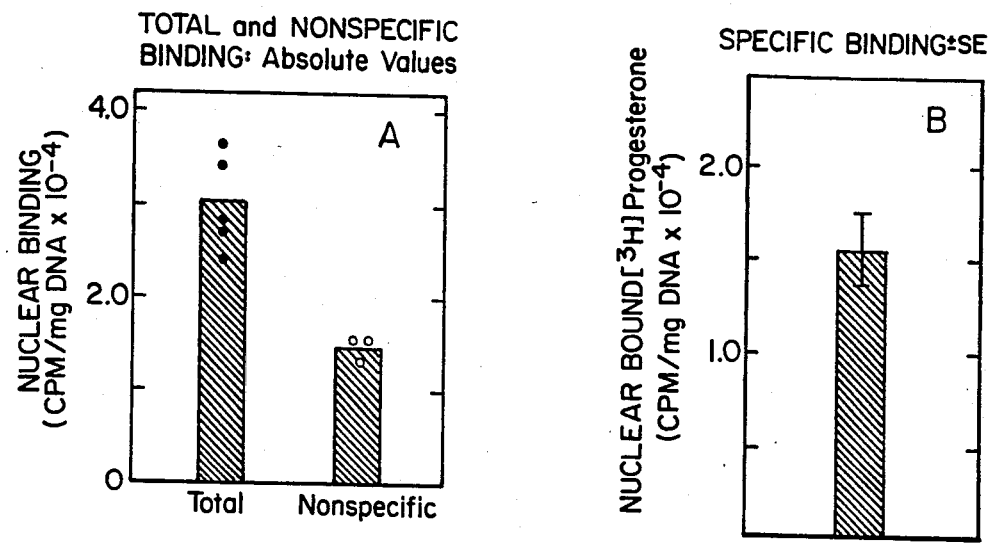

FIG. 8 shows that the nuclear binding assay is reproducible. Panel A summarizes the results of five separate assays which were performed for total binding (containing [³H] steroid only). Each assay consisted of two incubations. From this value is subtracted the value obtained for the nonspecific binding (an assay containing [³H] steroid + 100-fold unlabelled steroid) to give a specific binding shown in Panel B. The standard error of the calculated specific binding was ±10% S.E. of the mean.

Figure 9:
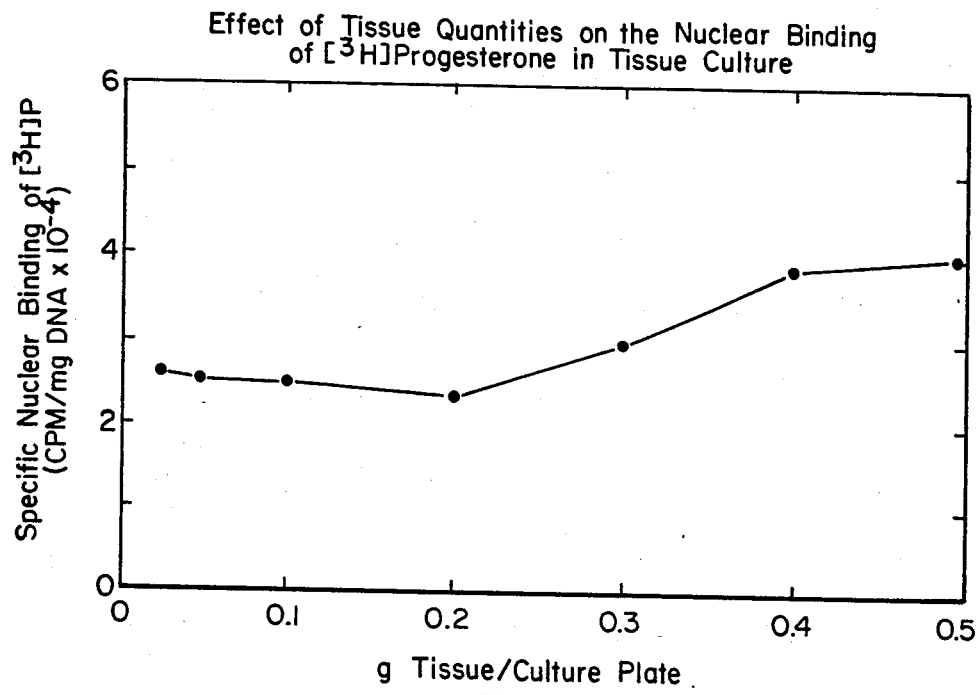

The effects of varying the quantities of the tissue on the amount of the nuclear radioactivity measured was also studied. FIG. 9 shows that 25 to 300 mg quantities of normal endometrium result in similar values for nuclear binding. Breast cancer biopsies using the present assay with the cell culture approach displayed the same properties of nuclear binding of [³H] estradiol as did the studies described here using normal endometrium.

Figure 10:
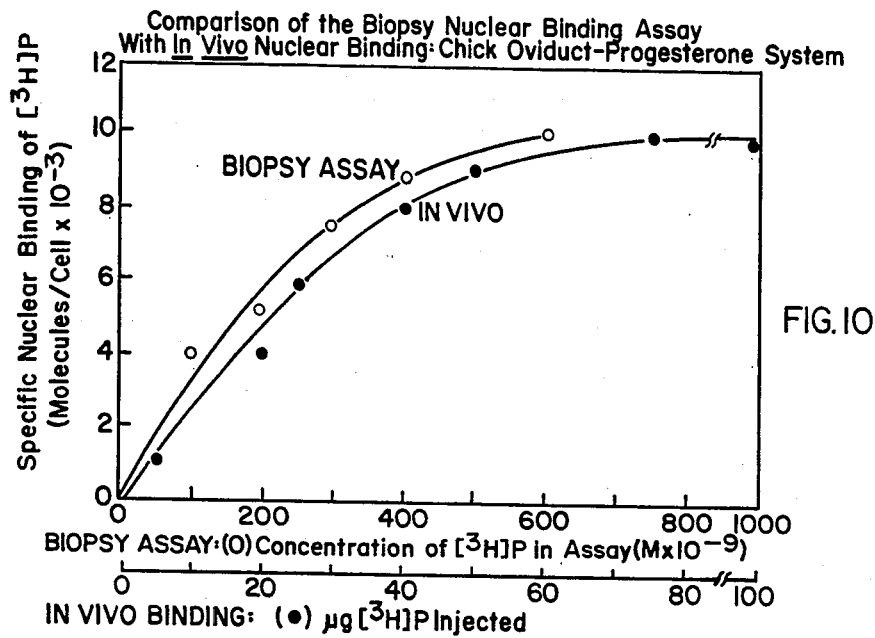

The chick oviduct was used as model system to determine whether or not the nuclear binding using the BNB assay is similar to the nuclear binding in vivo. The immature chick (7 days old) received daily injections of diethylstilbestrol (DES), 5 mg per injection, for 4 to 20 days. The oviducts in the uninjected chicks are undifferentiated but gradually undergo development during the estrogen treatment. By days 16 to 20, the oviducts are fully developed. FIG. 10 shows a comparison of the nuclear binding between in vivo conditions and the BNB assay. As can be seen, the BNB assay shows similar levels of saturation of the nuclear binding as achieved in vivo.

Figure 11:
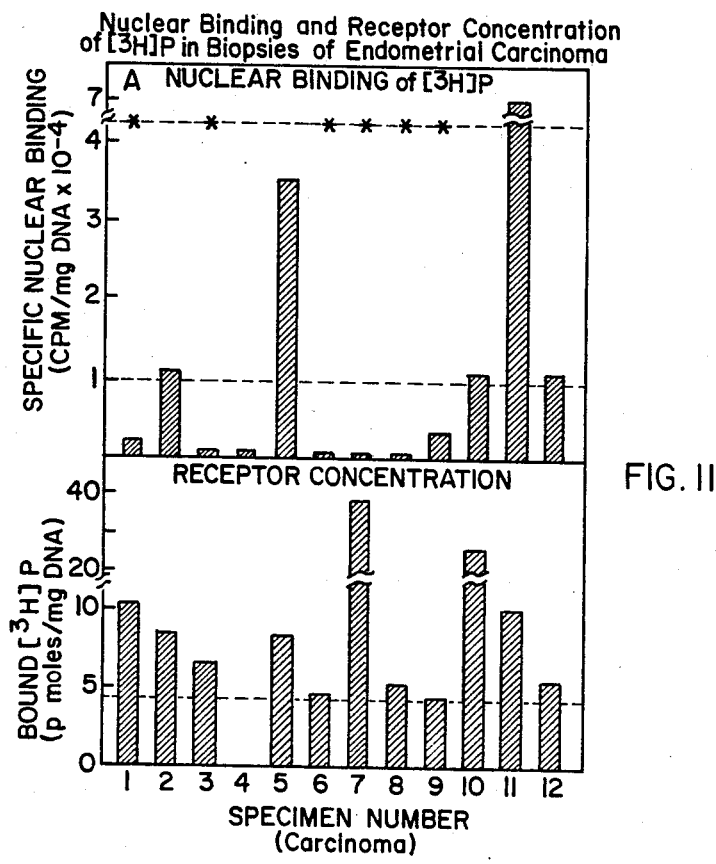

FIG. 11 shows the analysis of 12 patients with endometrial carcinoma. Panel A shows the results of the present BNB assay and Panel B the results of the conventional receptor quantitation assay (the Dextran charcoal absorption method). The conventional receptor quantitation assay (Panel B) indicates that 11 of the 12 patients have sufficient progesterone receptor to predict positive effects for therapy with this steroid. However, the assay of the present invention (Panel A) (the BNB assay) predicts only 5 of the 12 patients (42% of the total) will respond to this therapy. The reason for this discrepancy is that six patients (indicated by asterisks on Panel A) who have adequate PR, fail to display adequate nuclear binding of the steroid receptor. Thus, nonfunctioning receptors are indicated. More studies with the present assay have shown that of the 46 patients studied, only 17 (or 37%) of the total are predicted to respond to the progesterone therapy. Similar results have been obtained with breast cancer biopsies.

As determined by the assay of this invention, the amount of nuclear bound steroid or antisteroid gives the investigator a rapid indication as to how much "biologically active" receptor (i.e., receptor capable of binding to nuclear acceptor sites) is contained in the tumor in question (per mg DNA or per cell). It is therefore believed that this assay can as rapidly (within one day) and more accurately predict tumor response to a steroid or antisteroid compared to conventional receptor quantitation assays. Furthermore, the present assay requires about 10 times less tissue than those assays requiring receptor isolation and quantitation or than those which analyze receptor binding to isolated nuclei in a cell-free system. If desired, any excess tissue from the assay can be used to isolate the receptor for quantitative and qualitative analysis by conventional methods.

Nuclear binding defects may be primarily, if not totally, responsible for the failure of a wide variety of cancers to respond to steroid or antisteroid therapy. This would apply to such cancers as lung, breast, endrometrium, testicles, prostrate, lymphocytes and myelomas, as well as pituitary and ovary. Therefore, it is expected that the present assay will substantially enhance the clinician3 s ability to select the appropriate therapy to be employed which may be crucial to the effectiveness of the therapy selected.

The present assay is also expected to be useful to identify the presence or absence of functional steroid receptors in other, noncancerous pathological conditions in which steroid dependent cells are implicated. For example, the assay has positively identified functional progesterone receptors in lung tissue from a patient with pulmonary lymphangiomyomatosis. See M. L. Graham et al, *Mayo Clin. Proc.*, 59, 3 (1984), the disclosure of which is incorporated by reference herein.

The invention has been described with reference to various specific and preferred embodiments and techniques. However, it should be understood that many variations and modifications may be made while remaining within the spirit and scope of the invention.

What is claimed is:

1. A method for rapidly assaying a tissue sample for nuclear antisteroid binding comprising:
    (a) fragmenting said tissue sample;
    (b) digesting said fragmented tissue with collagenase;
    (c) isolating the cells from said digested tissue;
    (d) incubating said cells with an amount of a radiolabelled antisteroid capable of complexing with and saturating the steroid receptors in said cells;
    (e) isolating the cellular nuclei;
    (f) measuring the bound radioactivity and the total DNA of said nuclei; and
    (g) comparing the amount of bound radioactivity and the total DNA to determine a measure of the total nuclear bound steroid receptors.

2. The method of claim 1 wherein the tissue sample is carcinoma tissue.

3. The method of claim 2 wherein the carcinoma is selected from the group consisting of breast, endrometrium, testicular, lung, myeloma and prostate.

4. The method of claim 1 wherein about 1-1000 mg of tissue is fragmented.

5. The method of claim 4 wherein the tissue is contacted with about 0.5-15 units of collagenase per mg of tissue.

6. The method of claim 1 wherein the isolated cells are incubated in a medium which is about 5-50 nM in radiolabelled antisteroid.

7. The method of claim 6 wherein the radiolabelled antisteroid is a radiolabelled antiestrogen.

8. The method of claim 1 wherein the nuclei are isolated by layering a homogenate of said incubated cells onto a cold, neutral, aqueous medium comprising sucrose, glycerol, octoxynol-9, tris(hydroxymethyl)amino-methane hydrochloride and KCl and centrifuging said layered medium to obtain a pellet of purified nuclei.

9. The method of claim 8 further comprising dispersing said pellet in a neutral solution comprising tris(hydroxymethyl)amino-methane hydrochloride and glycerol, and collecting the dispersed nuclei by filtration.

10. The method of claim 1 wherein the DNA of said nuclei is measured by a diphenylamine assay.

11. A method for rapidly assaying a cancerous tissue sample for nuclear antisteroid binding comprising:
    (a) obtaining a sample of cancerous tissue by biopsy;
    (b) fragmenting said tissue sample;
    (c) disrupting said fragmented tissue sample in contact with about 1-5 units of collagenase per mg of tissue;
    (d) isolating the cells from said tissue sample;
    (e) incubating said cells with an amount of a radiolabelled antisteroid capable of complexing with and saturating the steroid receptors in said cells;
    (f) homogenizing said incubated cells;
    (g) layering said homogenate onto a cold, neutral aqueous medium comprising sucrose, glycerol, octoxynol-9, tris(hydroxymethyl)amino-methane hydrochloride and KCl;
    (h) centrifuging said layered medium to obtain a pellet of purified nuclei;
    (i) measuring the bound radioactivity and the total DNA of said nuclei; and
    (j) comparing the amount of bound radioactivity and the total DNA to determine a measure of the total nuclear bound steroid receptors.

12. The method of claim 11 wherein about 1-25 mg of tissue are obtained by biopsy.

13. The method of claim 11 wherein about 1-5 mg of tissue are obtained by biopsy.

14. The method of claim 11 wherein said cells are incubated in medium comprising about 5-50 nM of the radiolabelled antisteroid.

15. The method of claim 14 wherein the cells are incubated for about 0.5-1.5 hr at about 18-37° C.

16. The method of claim 14 wherein step (h) further comprises dispersing the pellet of purified nuclei in a neutral aqueous solution comprising tris(hydroxymethyl)amino-methane hydrochloride and glycerol and collecting them.

17. A method for rapidly determining the presence of functional cellular steroid receptors by assaying a tissue sample for nuclear steroid binding comprising:
    (a) fragmenting said tissue sample into pieces containing intact cells;
    (b) digesting said fragmented tissue with collagenase;
    (c) isolating the cells from said digested tissue;
    (d) incubating said cells with an amount of a radiolabelled steroid or a radiolabelled antisteroid capable of complexing with and saturating said receptors;
    (e) isolating the cellular nuclei;
    (f) extracting the bound radioactivity from said nuclei and measuring the bound radioactivity;
    (g) measuring the total DNA of said nuclei; and
    (h) comparing the amount of bound radioactivity and the total DNA to determine a measure of the total nuclear bound steroid receptors.

18. The method of claim 17 wherein the tissue sample is carcinoma tissue.

19. The method of claim 18 wherein the carcinoma is selected from the group consisting of breast, endrometrium, testicular, lung, myeloma and prostate.

20. The method of claim 17 wherein said 1-1000 mg of tissue is fragmented.

21. The method of claim 17 wherein the tissue is contacted with about 0.5-15 units of collagenase per mg of tissue.

22. The method of claim 17 wherein the isolated cells are incubated in a medium which is about 5-50 mM in radiolabelled steroid or radiolabelled antisteroid.

23. The method of claim 22 wherein the radiolabelled steroid is [$^3$H]-progesterone or [$^3$H]-estradiol.

24. The method of claim 17 wherein the nuclei are isolated by layering a homogenate of said incubated cells onto a cold, neutral, aqueous medium comprising sucrose, glycerol, octoxynol-9, tris(hydroxymethyl)amino-methane hydrochloride and KCl and centrifuging said layered medium to obtain a pellet of purified nuclei.

25. The method of claim 24 further comprising dispersing said pellet in a neutral solution comprising tris(hydroxymethyl)amino-methane hydrochloride and glycerol, and collecting the dispersed nuclei by filtration.

26. The method of claim 17 wherein, in step (g), the nuclei are hydrolyzed with perchloric acid and reacted with diphenylamine.

27. The method of claim 17 wherein the DNA of said nuclei is measured by a method comprising treating said nuclei with a protease and ribonuclease, mixing the treated nuclei with ethidium bromide and measuring the fluorescence of said nuclei.

28. The method of claim 17 wherein the bound radioactivity is extracted from said nuclei with alcohol.

29. The method of claim 18 wherein the alcohol is ethanol.

30. A method for rapidly determining the presence of functional steroid receptors in cancerous cells comprising assaying a tissue sample for nuclear steroid binding comprising:
   (a) obtaining a tissue sample by biopsy;
   (b) fragmenting said tissue sample into pieces containing intact cells;
   (c) disrupting said fragmented tissue sample in contact with about 1-5 units of colagenase per mg of tissue;
   (d) isolating the cells from said tissue sample;
   (e) incubating said cells with an amount of a radiolabelled steroid or a radiolabelled antisteroid capable of complexing with and saturating said receptors;
   (f) homogenizing said incubated cells;
   (g) isolating the cellular nuclei;
   (h) extracting the bound radioactivity from said nuclei;
   (i) measuring the total DNA of said extracted nuclei; and
   (j) comparing the amount of bound radioactivity and the total DNA to determine a measure of the total nuclear bound steroid receptors.

31. The method of claim 30 wherein about 1-25 mg of tissue are obtained by biopsy.

32. The method of claim 31 wherein about 1-5 mg of tissue are obtained by biopsy.

33. The method of claim 30 wherein said cells are incubated in medium comprising about 10-30 nM [$^3$H]-progesterone or [$^3$H]-estradiol.

34. The method of claim 30 wherein the cells are incubated for about 0.5-1.5 hr at about 18°-37° C.

35. The method of claim 13 wherein, in step (i), the nuclei are hydrolyzed with perchloric acid and reacted with diphenylamine.

36. The method of claim 30 wherein the bound radioactivity is extracted with absolute ethanol.

37. The method of claim 36 wherein said absolute ethanol comprises sodium acetate.

* * * * *

UNITED STATES PATENT AND TRADEMARK OFFICE
CERTIFICATE OF CORRECTION

PATENT NO.  : 4,806,464
DATED       : February 21, 1989
INVENTOR(S) : Thomas C. Spelsberg It is certified that error appears in the above-identified patent and that said Letters Patent is hereby corrected as shown below:

At Col. 1, line 36, for "extrogen" read --estrogen--.

At Col. 1, line 56, delete "TCS".

At Col. 2, line 58, delete "the functionality of".

At Col. 3, line 40, for "mineralcorticoid" read --mineralocorticoid--.

At Col 3, line 65, insert a bracket before the second "4", at the end of the line insert --phenyl]ethylene--.

At Col. 4, line 8, for "napthalene-type" read --naphthalene-type--.

At Col. 9, lines 40-41, for "nuceotides" read --nucleotides--.

At Col. 11, line 1, for "bond" read --bound--.

At Col. 15, line 26, for "18" read --28--.

Signed and Sealed this

Twentieth Day of March, 1990

*Attest:*

JEFFREY M. SAMUELS

*Attesting Officer*  *Acting Commissioner of Patents and Trademarks*